(12) United States Patent
Mikkelsen et al.

(10) Patent No.: US 6,277,097 B1
(45) Date of Patent: *Aug. 21, 2001

(54) INJECTION SYSTEM

(75) Inventors: Soren Mikkelsen, Ballerup; Lars Peter Klitmose, Gentofte; Andre Larsen, Dragør, all of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/045,314

(22) Filed: Mar. 20, 1998

Related U.S. Application Data

(60) Provisional application No. 60/047,930, filed on May 30, 1997.

(30) Foreign Application Priority Data

Mar. 25, 1997 (DK) .................................................. 0339/97
May 5, 1997 (DK) .................................................. 0513/97

(51) Int. Cl.⁷ .................................................. A61M 5/00
(52) U.S. Cl. .......................................... 604/187; 604/195
(58) Field of Search .................................... 604/186, 200, 604/201, 202, 206–211, 232, 195, 187, 415, 82, 87

(56) References Cited

U.S. PATENT DOCUMENTS

| | | | |
|---|---|---|---|
| 3,336,924 | 8/1967 | Sarnoff et al. . | |
| 4,710,178 | * 12/1987 | Leonard et al. | 604/209 |
| 5,279,586 | * 1/1994 | Balkwill | 604/207 |
| 5,358,489 | * 10/1994 | Wyrick | 604/136 |
| 5,599,323 | * 2/1997 | Bonnichsen et al. | 604/272 |
| 5,634,909 | * 6/1997 | Schmitz | 604/196 |
| 5,695,472 | * 12/1997 | Wyrick | 604/136 |
| 5,788,677 | * 8/1998 | Botich et al. | 604/195 |

FOREIGN PATENT DOCUMENTS

WO 92/11897   7/1992   (WO).

* cited by examiner

*Primary Examiner*—Anhtuan T. Nguyen
*Assistant Examiner*—Kevin C. Sirmons
(74) *Attorney, Agent, or Firm*—Skadden, Arps, Slate, Meagher & Flom LLP

(57) ABSTRACT

An injection system for preparing a mixture of a solvent and a medicament and for subsequent dosed injection of the mixture comprises a syringe accommodating an ampoule (7) in which a liquid is stored between a membrane (8) dosing one end of the ampoule (7) and a piston (6) which can by a piston rod (3) be forced into the ampoule (7) to press out a dose of the liquid. The piston rod (3) and the piston (6) has mutual engaging threads (4, 5) by which the piston (6) is coupled to the piston rod (3) to follow this rod in both axial directions. An outer thread (30) engaging an inner thread (29) in a housing is provided on a part (28) of the piston rod (3) so that rotation of the piston rod (3) will screw this rod and the piston (6) into the ampoule (7). A detent (18) ensures that the piston rod (3) is only rotated in a dose administering direction. However, the thread (30) of the piston rod (3) can be disengaged from the thread (29) of the housing to set the piston rod (3) free to be moved in a proximal direction.

6 Claims, 3 Drawing Sheets

Figure 6:
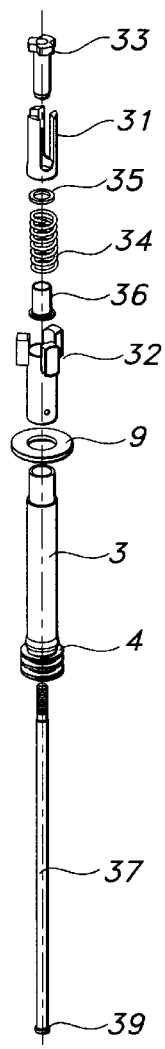

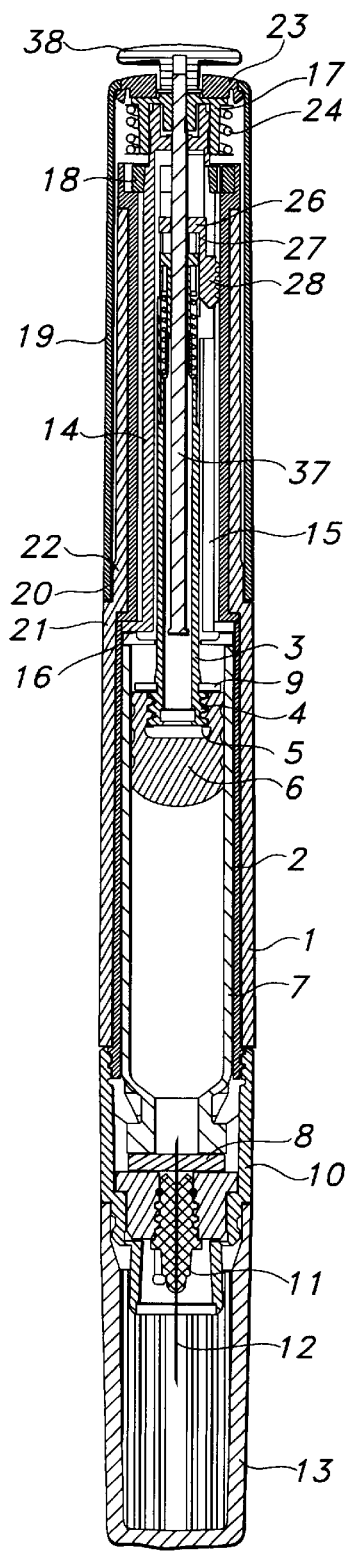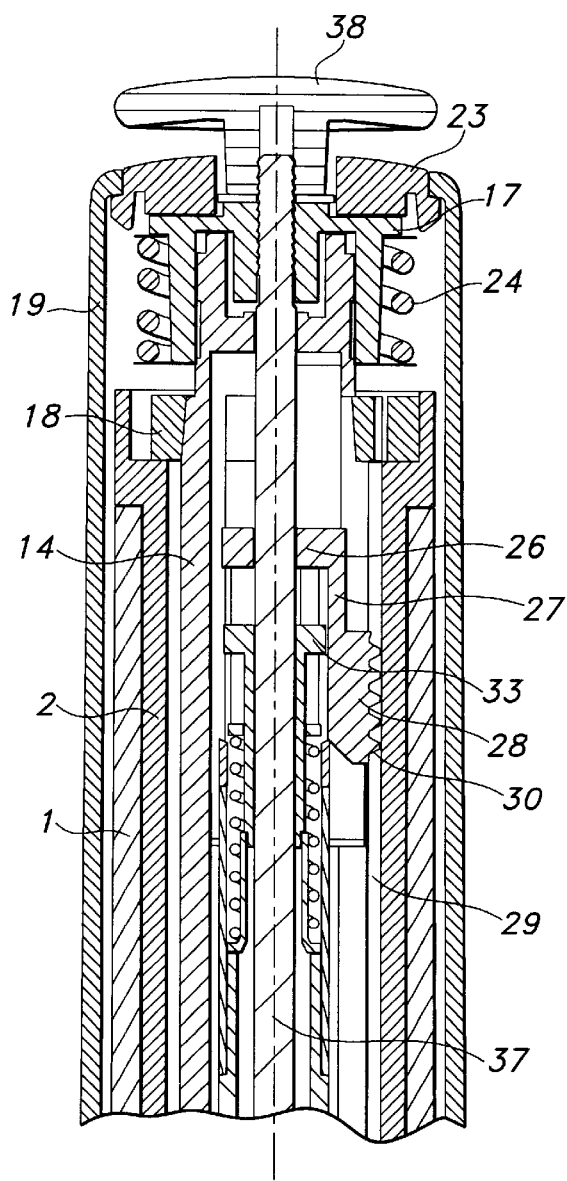
FIG 1
FIG 2

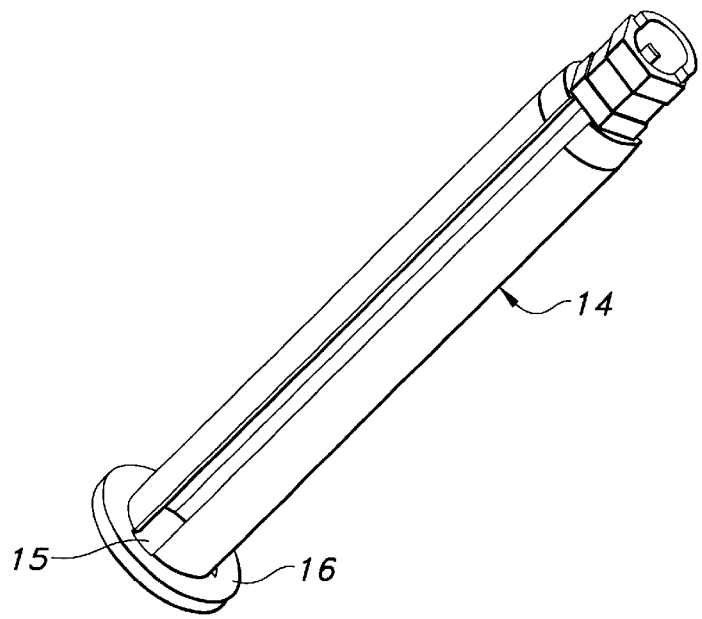
FIG 3
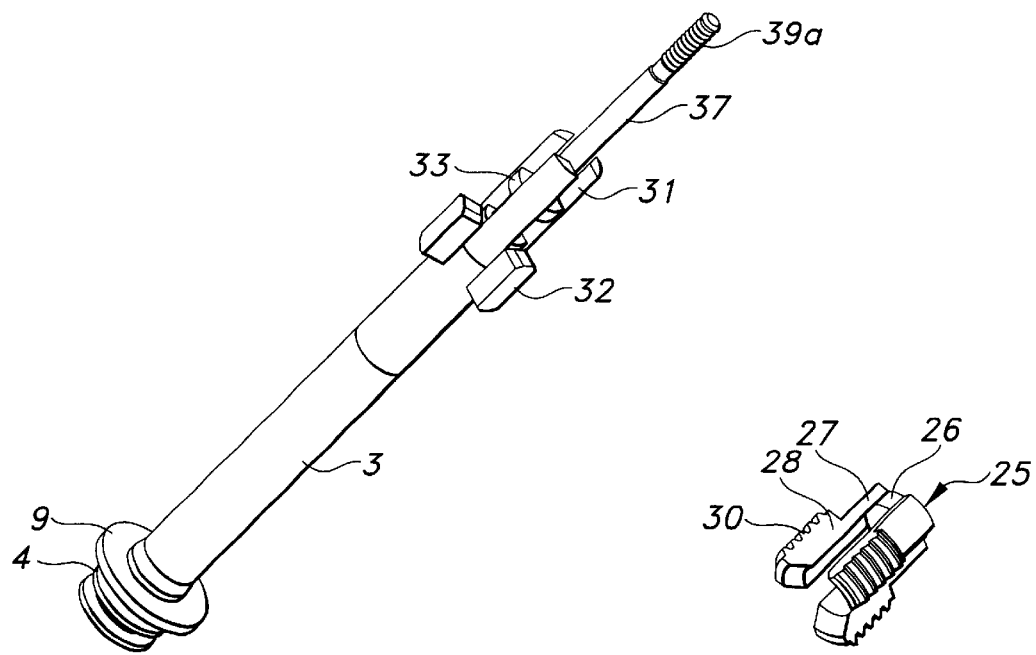
FIG 4          FIG 5

INJECTION SYSTEM

CROSS-REFERENCE TO RELATED APPLICATIONS

This application claims priority under 35 U.S.C. 119 of Danish applications 0339/97 filed Mar. 25, 1997 and 0513/98 filed May 5, 1997, and U.S. provisional application 60/047,930 filed May 30, 1997 the contents of which are fully incorporated herein by reference.

The invention relates to an injection system for preparing a mixture of a solvent and a medicament and for subsequent dosed injection of the mixture, the system comprising:

a syringe from which set doses are apportioned from a cylinder ampoule having a first end closed by a pierceable membrane and a second end closed by a piston which can by a piston rod, which is successively advanced in a distal direction by the injection of set doses, be forced into the ampoule to press out a dose of a medicament stored in the ampoule between the membrane and the piston through an injection needle piercing the rubber membrane, an ampoule with a solvent fitting into the syringe, and a needle mounted in a needle hub and having an injection part projecting from a distal side of the hub and a back needle piercing the membrane of an ampoule when the needle hub is mounted on the syringe.

Whereas many medicaments are supplied as a solution or a suspension in pre-filled cylinder ampoules of the kind mentioned above, some kinds of medicine have a low storability once they are dissolved. Therefore these types of medicine are mainly stored in a vial as a lyophilised powder which is dissolved in a solvent which is injected in the vial by the user immediately before he is going to load his syringe with a new ampoule. The solution obtained in the vial is transmitted to a cylinder ampoule which is then ready to be mounted in a syringe of the above mentioned kind.

By the mixing it is important that a precisely measured amount of solvent is used for dissolving the powder in the vial as else the concentration of the mixture in the ampoule will be wrong so that the user loses control of his medication. A precise mixing may be obtained by storing the solvent in the cylinder ampoule which is going to be used for the mixture. From the manufacturer the ampoule may contain a very precise amount of solvent which may be injected into the vial through a double ended needle penetrating the closing membranes of as well the ampoule as the vial.

When the powder in the vial is dissolved in the solvent injected in the vial, mixture obtained is sucked back into the ampoule by drawing the piston of this ampoule outward. If less than the total amount of solvent was injected into the vial, the remaining solvent will be mixed up in the mixture of medicine and solvent transmitted from the vial back into the ampoule.

When the piston of the ampoule is drawn outward to suck up the mixture in the ampoule it is very important that the piston is not drawn out of the ampoule as it may be difficult to put back again an as it will inevitably cause spill and contamination of the medicament.

From WO 95/12425 is known a device for filling a cylinder ampoule for use in a syringe of the above mentioned kind. This apparatus comprises a holder in which an ampoule containing a measured amount of solvent may be mounted. At its front end the holder is equipped with a connecting device coupling the outlet end of the ampoule to a vial into which the solvent shall be injected to dissolve a lyophilised medicament. To the rear end of the holder a support is mounted In which a piston rod may be moved in the axial direction of the ampoule. The distal end of the piston rod is screwed into the piston and the proximal end of the piston rod projects from said support. The solvent in the ampoule may be pressed through a needle which from the front end of the ampoule forms a channel to the interior of the vial. The solvent is transmitted from the ampoule to the vial by pressing the projecting end of the piston rod which then presses the piston into the ampoule. The mixture obtained in the vial is thereafter sucked back into the ampoule by drawing the piston outward. This outward drawing is made possible by the fact that a rear end of the piston is provided with a hole with an inner thread which is engaged by an outer thread at the distal end of the piston rod. The piston rod support which forms a stop preventing the piston from being drawn out of the ampoule is fixed to the ampoule holder in such a way that it cannot be unfixed unless the screw connection between the piston and the piston rod is brought out of engagement. This way the risk for inadvertently drawing out the piston is eliminated.

However, the described solution implies that different devices must be carried and used. First the filling device must be taken apart and the ampoule mounted into said device. Then a filling procedure must be run through. Thereafter the device must be taken apart again to remove the filed ampoule, which must then be installed in the syringe by which a dose may be set and injected.

Consequently it is an object of the invention to provide an injection system which makes a special filling device superfluous.

This is obtained by a system of the kind mentioned in the opening of this application, which system is characterised in that the piston rod of the syringe and the piston of the ampoule has co-operating coupling means by which the piston of the ampoule is secured to the piston rod of the syringe to make said piston follow movements of the piston rod in both axial directions.

In such a syringe an ampoule with solvent may be mounted with the distal end of the piston rod engaging the piston of the ampoule, and through a needle mounted in the common way on the syringe the solvent may be injected into a vial by repetitively setting a dose and injecting this dose through the closing rubber membrane of the vial until the ampoule is emptied. An adapter may be mounted between the syringe and the vial to keep these elements in position during said operation and during the next operation which is to draw the piston rod in a proximal direction whereby it due to its engagement with the piston in the ampoule will draw this piston outward in the ampoule. Thereby the mixture prepared in the vial by the injection of the solvent will be sucked into the ampoule from where it may now be apportioned in doses which may be individually set by the dose setting mechanism.

The coupling means of the piston rod and the piston may appropriately be parts of which one carries an outer thread which can engage an inner thread in the other part. However other kinds couplings allowing transmission of axial movements in both axial direction may be used so as snap couplings or bayonet couplings. In some syringes the piston may be moved in both axial directions against the resistance of friction in a piston rod guidance whereas other syringes are provided with a unidirectional coupling which allows only a movement of the piston rod and the piston in a distal direction when an ampoule is mounted in the syringe. When the ampoule is dismounted the unidirectional coupling is released and the piston rod may be moved in the proximal direction to a retracted position which it takes up when a full ampoule is mounted. In such syringes means may be provided which even when an ampoule is mounted in the syringe can be operated to set the piston free to be moved in a proximal direction.

According to a preferred embodiment of the invention he dosing mechanism of the syringe comprises a dose setting and injecting member which to set a dose is rotated from a stop an angle which is proportional with the set dose and which to inject the set dose is rotated back to the stop, an inner thread in a tubular housing of the syringe, an outer thread provided on elements forming a part of a piston rod assembly, which outer thread is in engagement with the inner thread of the housing, a unidirectional coupling between the dose setting and injecting member which only by injecting transmits the rotation to the piston rod to screw this rod in a distal direction through the housing, which syringe may according to the invention be characterised in that the means setting the piston rod free are means drawing the elements carrying the external thread out of engagement with the inner thread of the housing. In such a syringe the means setting the piston rod free may be means drawing the elements carrying the external thread of the piston rod out of engagement with the inner thread of the housing.

An ampoule according to the invention is an ampoule designed to fit into a syringe for apportioning of set doses and which ampoule has a piston provided with coupling means designed for co-operation with coupling means on the piston rod of said syringe to secure said piston to said piston rod.

In the following the invention is described in further details with reference to the drawing, wherein FIG. 1 shows a sectional view of a syringe according to the invention, FIG. 2 shows in an enlarged scale the proximal part of the syringe shown in FIG. 1.

Figure 7:
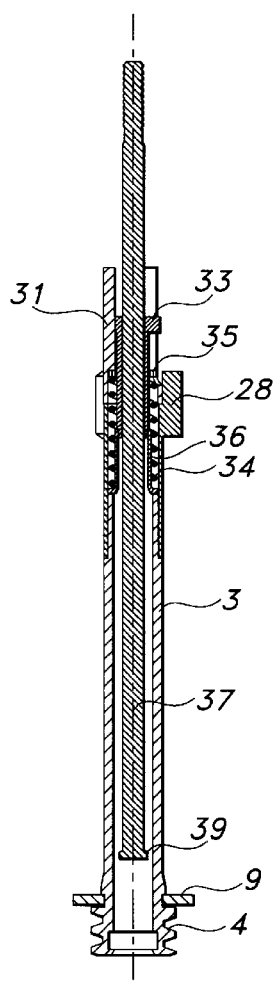
Figure 8:
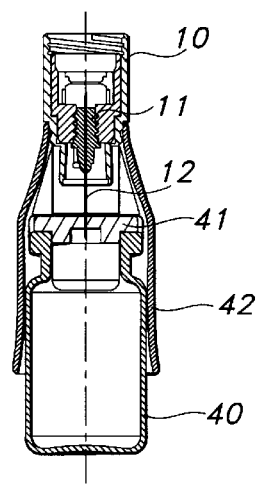

FIG. 3 shows a perspective view of a carrier in the syringe according to FIGS. 1 and 2, FIG. 4 shows perspective view of a piston rod assembly for the syringe shown in FIGS. 1 and 2, FIG. 5 shows a perspective view of a piston rod driver for the syringe shown in FIGS. 1 and 2, FIG. 6 shows an expanded view of the piston rod assembly shown in FIG. 4, FIG. 7 shows a sectional view of the piston rod assembly, and FIG. 8 shows the distal end of a syringe coupled to a vial.

The syringe in FIG. 1 has a tubular housing 1 with an inner tubular housing 2. The distal ends of the end of the housings form a cartridge holder and the proximal ends accommodate mechanisms by which mixing of a medicament, dose setting and injection are controlled.

A piston rod 3 is at its distal end provided with an outer thread 4 which fits into an inner thread 5 in a piston 6 of an ampoule 7 which is at its distal end closed by a membrane 8. By mounting of the ampoule this ampoule is rotated so that the thread 4 of the piston rod 3 engages the thread 5 of the piston in the ampoule 7. A flange 9 near the distal end of the piston rod 3 defines the distance the piston rod 3 may be screwed into the piston 6 so at the piston rod 3 is not wedged in the piston 6. Her the connection between piston and piston rod is shown as a thread connection but other connections so as bayonet couplings may be used to secure the piston to the piston rod in such a way that the piston will follow the piston rod during axial movements thereof in both directions.

When the piston 3 of the ampoule 7 is attached to the piston rod 3 the cartridge holder is closed by an end stopper 10 screwed on the distal end of the inner housing 2. The membrane 8 of the ampoule is sealed on this ampoule by a member having a threaded opening in which a needle hub 11 with a double pointed needle 12 may be received so that one end of the needle 12 penetrates the rubber membrane 8 of the ampoule 7 whereas the other end of the needle may be inserted through the skin of a person who shall receive an injection. When the syringe is not in use the needle receiving part with the needle may be covered by a cap 13 so that nobody is hurt by the needle.

In its withdrawn position as shown in FIG. 1 the piston rod 3 is accommodated in the proximal part of the inner housing where it is surrounded by a carrier 14 which is shown in FIG. 3 and is a longitudinal tubular member having three longitudinal slots 15 in approximately its full length and a flange 16 at its distal end. At its proximal end the carrier 14 has a part with a not round cross section and which is snapped into a correspondingly not round opening in a driver 17 through which rotation is transmitted to the carrier during injection operation of the syringe as it will be described be low. The carrier 14 may be rotated about its axis but a ratchet 18 coupled between the carrier 14 and the inner housing 2 has the effect that the carrier is rotatable in only one direction.

The proximal part of the housing 1 is surrounded by a cap 19 which may rotate on said proximal part. An edge of the cap 19 is provided with a dose indicating scale 20 which may by rotation of the cap be moved relative to an arrow 21 on the housing 1 at the transition between the proximal and the distal part. A protrusion 22 on outer wall of the housing 1 provides a stop against which a not shown protrusion in the cap abuts. When the cap is rotated in a direction away from the stop a circular surface with saw tooth shaped steps having a steep and an inclined edge provided on the inner side of the end bottom 23 of the cap 19 slides over a corresponding surfaced provided on the driver 17. The surfaces are forced against each other by a spring 24 so that a click is heard each time the top of the steps on one of the surfaces fall down in the bottom of the steps on the other surface. When the cap is rotated back until its protrusion abuts the stop 22 on the outer wall of the housing 1 the end bottom 23 will transmit the rotation to the driver 17 as the steep edge of the steps on the circular surfaces of the end bottom 23 will now abut the steep edges of the steps on the driver 17. The driver 17 is then rotated and is rotation is transmitted to the carrier 14 the ratchet 18 being so oriented that it allows this rotation.

FIG. 5 shows a piston rod driver 25 comprising a disc 26 from the edge of which three 120° displaced flexible arms 27 extend in an axial direction. At the outer ends of the arms 27 members 28 are provided each carrying a thread 30 which may engage a matching thread 29 on the inner side of the proximal part of the inner housing 2 when the members 28 are supported so that the flexible arms 27 do not bend away so that the threads 30 and 29 are disengaged.

The piston rod 3 which at its distal end is provided with the tread 4 for engagement with a thread in the piston 6 of an ampoule is a part of a piston rod assembly which is shown in FIGS. 4, 5 and 6 in perspective, as an expanded view, and a sectional view respectively. The piston rod 3 is tubular and is at its proximal end provided with three axial, 120° displaced slots dividing the end of the piston rod into three tongues 31. At the bottom end of each of the slots the piston rod is provided with a protrusion 32 which engages the slots 15 of the carrier 14. The piston rod driver 25 is mounted with its disc 26 abutting the end of the tongues 31, its arms 27 engaging the slots between the tongues 31, and the free ends of its threaded members 28 abutting the proximal ends of the protrusions 32. The protrusions 32 and the threaded members 28 of the piston rod driver protrude through the slots 15 of the carrier and this way rotation of the carrier will be transmitted to the piston rod 3 and the piston rod driver 25 whereas piston rod 3 and piston rod driver 25 may be axially displaced relative to the carrier 14. A support member having protrusions 33 engaging the slots between the tongues 31 of the piston rod 3 is against the force of a spring 34 axially displaceable in the piston rod 3 from a position near the distal end of said slots to a position near the free end of the tongues 31. In the position near the bottom end of the slots the protrusions 33 will support the members 28 and keep their threads 30 in engagement with the thread 29 of the housing, but when the protrusion are moved to their position near the end of the tongues 31 the arms 27 of the piston rod driver is supported near the disc 26 and the members 28 may due to the oblique sides of the engaging threads 29 and 30 be pressed inward toward the axis so that they may be moved axially with their threads 30 scratching over the thread 29 in the housing.

FIG. 6 shows an expanded view of the piston rod assembly. It is seen that the piston rod assembly is provided by combining a tubular part forming the actual piston rod 3 and provided with a thread 4 the active length of which is limited by a flange 9 provided by a ring mounted on the piston rod. The protrusions 32 are provided on a part 35 added to form a part of the piston rod 3. The same way the slotted part of the piston rod is added as an individual part. Between the slotted part an the rest of the piston rod a ring 35 is mounted forming an abutment for the spring 34 which is inserted between said ring and a flange on a tubular sleeve 36 in which an end of the supporting element is secured. A spindle 37 extends all the way through the piston rod, the supporting element and the disc of the piston driver and has at its distal end a head 39 having a diameter which is larger than the diameter of the bore in the sleeve 36 so that this head will engage the flanged end of the sleeve 38 if the spindle is drawn in the proximal direction and will against the force of the spring 34 move the supporting element on which the sleeve 36 is secured to a position wherein its protrusions lies near the free ends of the tongues 31. The spindle 37 further projects through the driver 17, the end bottom 23 of the cap 19 and into a button 38. By a thread 39a the spindle is secured to the driver 17 and to the button 38 whereas the diameter of the opening through the end bottom 23 of the cap 19 is large enough to let the spindle 37 pass freely.

Due to the ratchet 18 the carrier may only be rotated in a direction by which the piston driver is rotated relative to the housing in such a direction that said piston driver is screwed in a direction towards the distal end of the syringe to press out the content of an ampoule mounted in the syringe. A dose may therefore be set by rotating the cap away from the stop 22 in the opposite direction to make the coupling between the driver 17 and the end bottom 23 of the cap 19 click over a number of teeth corresponding to the size of the wanted dose this way giving an audible indication of the size of the set dose. During the clicking the button 6 will sink and jump back at each click to give a tactile indication of the size of the set dose. Thereafter the set dose may be injected by rotating the cap 19 back to abutment with the stop. During this rotation the coupling between the end bottom of the cap and the driver 17 will transmit the rotation to the driver 17 which will again rotate the carrier 14 which transmits the rotation to the piston driver to screw it along the housing 2 a distance proportional with the angle of rotation.

When the syringe is going to be used for injection of a medicament which has to be mixed from two or more components immediately before the use, an ampoule with a solvent component is mounted in the syringe, a needle is mounted and the free end of this needle is inserted in a vial containing another possibly solid component of the medicament. In FIG. 8 this insertion is illustrated by a vial 40 which is closed by a stopper 41 through which the needle 12 is inserted. It is further illustrated how an adapter 42 may be placed on the vial 40 which adapter has a socket to which the distal end of the syringe may be mounted using the coupling which normally is used for fixing the needle protection cap 13. With the needle inserted in the vial repetitive dose setting and injection rotations of the cap is performed whereby the piston is successively moved into the ampoule until the full content thereof is injected into the vial 40.

Hereafter the vial may be turned upside down still with the needle inserted through the stopper of the vial. Now the piston in the ampoule may be drawn back to its position corresponding to a full ampoule whereby the mixture provided in the vial may be sucked back into the ampoule. This is obtained by drawing the cap in a proximal direction which means that the spindle 37 is pulled in this direction. Hereby the driver which is secured to the spindle and snap locked onto the carrier 14 will first be lifted off said carrier where after the spindle may be moved freely until its head 39 abuts the sleeve 36. Further movement of the spindle 37 will cause a compression of the spring 34 and the protrusions of the support member will be moved to their position near the free end of the tongues 31 where the piston threaded members 28 of the piston driver 25 is no longer supported. The axial pull of the spindle is now transmitted to the piston rod which is restrained in moving due to the engagement between the inner thread in the housing and the threaded members 28 of the piston drive. However, due to the lacking support of the members 28 these may be bend inward towards the axis and the engagement between the threads 29 and 30 may be released so that the piston rod 3 may be drawn backward with the piston drive members scratching over the thread 29 in the housing. Due to the engagement between the thread 4 at the distal end of the piston rod 3 and the thread in the piston 6 of the ampoule 7 said piston is drawn outwards in the ampoule and the content from the vial 40 is sucked over into the ampoule 7. When the spindle 37 thereafter is moved back to its original position the spring 34 is released and the support member is moved back so that its protrusions 33 support the threaded members of the piston rod driver 25 to keep the tread of these members in engagement with the inner thread 29 of the housing. Finally the driver 17 is snapped onto the carrier 14 again and the syringe is ready for use as a syringe by which a dose may be set and injected.

In the syringe described the piston rod is bound to be moved in the distal direction by the dosing mechanism due to the ratchet 18 which provides a one way coupling which ensures that the piston rod is only movable in said distal direction as long as it is coupled to the dosing mechanism. In other types of syringes the piston rod is prevented from being moved in a proximal direction by detent mechanisms comprising a pawl which secured to the housing engages a toothing along the piston rod or comprising a leaf spring which secured to the housing cuts into the piston rod. To realise the invention such a pawl engagement or cutting engagement may by appropriate members be operated to be disengaged to set the piston free to be moved in a proximal direction.

In the above description the mutual engaging threads of the piston rod and the piston are provided as an outer thread at the end of the piston rod which engage an inner thread in a bore in the piston. Alternatively the piston can be provided with a threaded stud engaging an inner thread in a bore in the end of the piston rod.

What is claimed is:

1. An injection system for use in preparing a mixture of a solvent and a medicament and for subsequent dosed injection of the mixture, the system comprising a syringe having a housing with proximal and distal ends, and a replaceable ampoule secured relative to the syringe housing, wherein the ampoule includes a first end closed by a pierceable membrane, a second end closed by a piston having a first coupling element, and a solvent stored between the membrane and piston; and wherein the syringe comprises:

means located at the distal end of the housing for mounting a disposable needle;

a piston rod which is supported in the housing for axial movement and which includes a second coupling element which detachably couples the piston rod to the piston, such that the piston follows movement of the piston rod in both axial directions;

a dose setting and injection mechanism supported by the housing for setting doses and for advancing the piston rod in a distal direction to inject a set dose;

a disengageable coupling between the housing and the piston rod to allow movement of the piston rod in the distal direction by means of the dose setting and injection mechanism to eject solvent from the ampoule to mix with a medicament, but to prevent movement of the piston rod in a proximal direction, when an ampoule is secured to the syringe; and a release mechanism which can be activated for selectively releasing the disengageable coupling between the piston rod and the housing while an ampoule is secured to the syringe to allow the piston rod to move in the proximal direction to suck back a mixture into the ampoule, and deactivated to re-engage the disengageable coupling to make movement of the piston rod depend on the dose setting and injection mechanism to prepare the system for injecting such mixture.

2. A system according to claim 1, wherein the first and second coupling elements comprise threads.

3. A system according to claim 1, wherein the syringe housing includes a stop, wherein the dose setting and injection mechanism includes a member which abuts the stop to limit the movement of the piston rod in the distal direction, wherein the member can be rotated in a first rotational direction away the stop to set a dose, the angle of rotation being proportional to the dose set, and wherein the member, to inject the dose, can be rotated in a second rotational direction back into engagement with the stop.

4. A system according to claim 1, wherein the syringe housing has an inner thread, wherein the disengeable coupling includes a driver element having an outer thread which selectively engages the inner thread, and a unidirectional coupling between the dose setting and injection member and the piston rod which coupling transmits rotation of the dose setting and injection member to the piston rod only when the member rotates in the second rotational direction, wherein the driver element, responsive to being rotated in the second rotational direction, moves the piston rod in the distal direction, and wherein the release mechanism is coupled to the driver element to allow the thread of the driver element to be drawn out of engagement with the inner thread of the syringe housing to allow the piston rod to be moved in a proximal direction.

5. A method of preparing a mixture of a solvent and a medicament and for subsequent dosed injection of the mixture, comprising the steps of:

providing a syringe having a housing with proximal and distal ends, a piston rod which is supported in the housing for axial movement, a dose setting and injection mechanism supported by the housing for setting doses and for advancing the piston rod in a distal direction to inject a set dose, a disengageable coupling between the housing and the piston rod to allow movement of the piston rod in the distal direction, but to prevent movement of the piston rod in the proximal direction, when an ampoule is secured to the syringe, and a release mechanism for selectively releasing the disengageable coupling between the piston rod and the housing, while an ampoule is secured to the syringe, to allow the piston rod to move in the proximal direction;

securing a replaceable ampoule relative to the syringe housing, wherein the ampoule includes a first end closed by a pierceable membrane, a second end closed by a piston having a first coupling element, and a solvent stored between the membrane and piston;

detachably coupling the first coupling element to a second coupling element on the piston rod, such that the piston follows movement of the piston rod in both axial directions;

ejecting the solvent from the ampoule using the dose setting and injection mechanism;

mixing the ejected solvent with a medicament; and sucking the mixed solvent and medicament back into the ampoule by actuating the release mechanism and moving the piston rod in a proximal direction.

6. A method according to claim 5, wherein the first and second coupling elements are threads and the coupling step is performed by screwing the coupling elements together.

* * * * *